(12) United States Patent
Hendriks et al.

(10) Patent No.: US 8,702,612 B2
(45) Date of Patent: Apr. 22, 2014

(54) CATHETER FOR THREE-DIMENSIONAL INTRACARDIAC ECHOCARDIOGRAPHY AND SYSTEM INCLUDING THE SAME

(75) Inventors: Bernardus Hendrikus Wilhelmus Hendriks, Eindhoven (NL); Stein Kuiper, Neerijnen (NL); Jan Frederik Suijver, Dommelen (NL); Ronald Tabaksblat, Den Bosch (NL); Nijs Cornelis Van Der Vaart, Rosmalen (NL); Christopher Stephen Hall, Hopewell Junction, NY (US); Anna Teresa Fernandez, Falls Church, VA (US)

(73) Assignee: Koninklijke Philips N.V., Eindhoven (NL)

( * ) Notice: Subject to any disclaimer, the term of this patent is extended or adjusted under 35 U.S.C. 154(b) by 787 days.

(21) Appl. No.: 12/522,037

(22) PCT Filed: Jan. 10, 2008

(86) PCT No.: PCT/IB2008/050080
§ 371 (c)(1),
(2), (4) Date: Sep. 30, 2009

(87) PCT Pub. No.: WO2008/084455
PCT Pub. Date: Jul. 17, 2008

(65) Prior Publication Data
US 2010/0280390 A1 Nov. 4, 2010

Related U.S. Application Data

(60) Provisional application No. 60/884,481, filed on Jan. 11, 2007.

(51) Int. Cl.
*A61B 8/12* (2006.01)
*A61B 8/14* (2006.01)

(52) U.S. Cl.
USPC ........... 600/466; 600/463; 600/462; 600/459; 181/176

(58) Field of Classification Search
USPC ......................................................... 181/176
See application file for complete search history.

(56) References Cited

U.S. PATENT DOCUMENTS

| 5,477,736 | A | | 12/1995 | Lorraine |
| 5,507,294 | A | * | 4/1996 | Lum et al. ................. 600/459 |
| 5,682,895 | A | * | 11/1997 | Ishiguro .................... 600/440 |
| 5,713,363 | A | | 2/1998 | Seward et al. |
| 5,720,287 | A | | 2/1998 | Chapelon et al. |
| 5,795,299 | A | | 8/1998 | Eaton et al. |
| 5,846,205 | A | | 12/1998 | Curley et al. |
| 6,039,693 | A | | 3/2000 | Seward et al. |
| 6,306,096 | B1 | | 10/2001 | Seward et al. |
| 2006/0079728 | A1 | * | 4/2006 | Kuiper et al. ................ 600/9 |
| 2006/0106426 | A1 | * | 5/2006 | Campbell ..................... 607/3 |

FOREIGN PATENT DOCUMENTS

| WO | WO03069380 | 8/2003 |
| WO | WO2004051323 | 6/2004 |
| WO | WO2005122139 | 12/2005 |
| WO | WO2007125500 | 11/2007 |

* cited by examiner

*Primary Examiner* — Long V. Le
*Assistant Examiner* — Farshad Negarestan

(57) ABSTRACT

A catheter apparatus includes an elongated body having proximal and distal ends, and an acoustic transducer disposed proximate the distal end of the elongated body. A variably-refracting acoustic lens is provided to dynamically adjust a direction associated with an acoustic wave coupled to the acoustic transducer in response to one or more control signals provided thereto.

25 Claims, 5 Drawing Sheets

CATHETER FOR THREE-DIMENSIONAL INTRACARDIAC ECHOCARDIOGRAPHY AND SYSTEM INCLUDING THE SAME

CROSS REFERENCE TO RELATED CASES

Applicants claim the benefit of International Application Number PCT/IB2008/050080, filed Jan. 10, 2008, and Provisional Application Ser. No. 60/884,481, filed Jan. 11, 2007.

This invention pertains to catheters, and more particularly to intracardiac echocardiography (ICE) catheters and systems for three dimensional ICE.

Acoustic waves (including, specifically, ultrasound) are useful in many scientific or technical fields, such as medical diagnosis, non-destructive control of mechanical parts and underwater imaging, etc. Acoustic waves allow diagnoses and controls which are complementary to optical observations, because acoustic waves can travel in media that are not transparent to electromagnetic waves.

For example, intracardiac echocardiography (ICE) is becoming an important tool for diagnosis and treatment of many cardiac abnormalities such as endocarditis, atrial septal defects (ASD), patent foramen ovale (PFO), ventricular septal defects (VSD), left atrial appendage occlusion and the treatment of atrial fibrillation. Intracardiac echocardiography (ICE) has been used to guide radiofrequency catheter ablation procedures and transseptal punctures. Especially in atrial fibrillation during treatment procedures such as ablation it is very important to have good anatomical information of the interior of the heart. Combining ICE with the ablation process is extremely valuable for clinicians.

Toward this end, a number of ICE catheters have been developed.

For example, U.S. Pat. No. 5,713,363, entitled "Ultrasound catheter and method for imaging and hemodynamic monitoring," describes a catheter having a linear phased-array ultrasonic transducer mounted near the distal end of the catheter for flow measurements and imaging. Also disclosed is the use of a multiplane phased-array ultrasound transducer.

Meanwhile, U.S. Pat. No. 5,795,299, entitled "Ultrasonic transducer assembly with extended flexible circuits," describes an improved driver circuit for use with an ultrasonic transducer assembly that can be used within a body cavity.

Also, U.S. Pat. No. 5,846,205, entitled "Catheter-mounted, phased-array ultrasound transducer with improved imaging," describes a phased-array ultrasonic transducer at the distal end of a catheter, where the transducer is covered by an exit window that is essentially nonfocusing for ultrasound, allowing smaller sized catheter dimensions.

Additionally, U.S. Pat. No. 6,039,693, entitled "Volumetric image ultrasound transducer underfluid catheter," describes a volumetric, ultrasound transducer underfluid catheter system for generating three-dimensional images. It allows real-time three-dimensional images of underfluid features of tissues without frequently rotating, flexing or extending the catheter.

Furthermore, U.S. Pat. No. 6,306,096, entitled "Volumetric image ultrasound transducer underfluid catheter system," describes a method of viewing a cardiovascular underfluid structure with the device described in U.S. Pat. No. 6,039,693.

To summarize, ICE catheters including one-dimensional ("1D") and two-dimensional ("2D") phased array acoustic transducers for real-time two-dimensional and three-dimensional ultrasound imaging inside the body are described in the patent literature.

In equipment employing a one-dimensional acoustic transducer array, the acoustic transducer elements are often arranged in a manner to optimize focusing within a single plane. This allows for focusing of the transmitted and received acoustic pressure wave in both axial (i.e. direction of propagation) and lateral dimensions (i.e. along the direction of the 1D array).

A one-dimensional acoustic transducer array allows two-dimensional imaging of the interior of the heart. Although this two-dimensional information is valuable, the ability to position the ICE catheter with only two-dimensional information is limited. A three-dimensional view is required to be able to precisely guide the ablation device to the correct area in the heart.

Two-dimensional transducer arrays have been considered, as mentioned above, but these devices suffer from complicated electronics to drive the transducer, making these devices expensive. Furthermore, the dimensions of the transducer array, and all of the wires required to drive it, make it difficult to fit into the limited catheter space. The wires may also cause compatibility issue for magnetic resonance imaging (MRI). Catheters are typically employed in a single use scenario, therefore the price for the catheter and imaging assembly become quite important to the end user and manufacturer.

Accordingly, it would be desirable to provide an ICE catheter capable of providing a three-dimensional view of the interior of the heart without employing a two-dimensional ultrasound transducer array that suffers from high costs, complicated electronics, and MRI-compatibility issues. It would further be desirable to provide a method of obtaining a three-dimensional view of the interior of the heart employing an ICE catheter that does not require a complicated and expensive two-dimensional ultrasound transducer array.

In one aspect of the invention, a catheter apparatus comprises: an elongated body having proximal and distal ends; an acoustic transducer, disposed proximate the distal end of the elongated body, and a variably-refracting acoustic lens coupled to the acoustic transducer, the variably-refracting acoustic lens being adapted to adjust at least one acoustic signal processing characteristic thereof in response to a selected voltage applied thereto.

In another aspect of the invention, a catheter apparatus includes an elongated body having proximal and distal ends, and an acoustic transducer, disposed proximate the distal end of the elongated body, and further includes a variably-refracting acoustic lens adapted to dynamically adjust a direction associated with an acoustic wave coupled to the acoustic transducer, in response to one or more control signals provided thereto.

In still another aspect of the invention, a system includes a catheter, an acoustic signal processor, and a voltage generator. The catheter includes an elongated body having proximal and distal ends, an acoustic transducer, disposed proximate the distal end of the elongated body, and a variably-refracting acoustic lens coupled to the acoustic transducer, the variably-refracting acoustic lens being adapted to adjust at least one acoustic signal processing characteristic thereof in response to a selected voltage applied thereto. The acoustic signal processor is coupled to the acoustic transducer of the catheter, and the voltage generator is adapted to apply the selected voltage to the variably-refracting acoustic lens of the catheter.

FIG. 1 shows one embodiment of an ICE catheter.

FIGS. 2A-B show a perpendicular cross section view of one embodiment of an ICE catheter including an acoustic transducer in combination with a variably-refracting acoustic lens.

Figure 1:
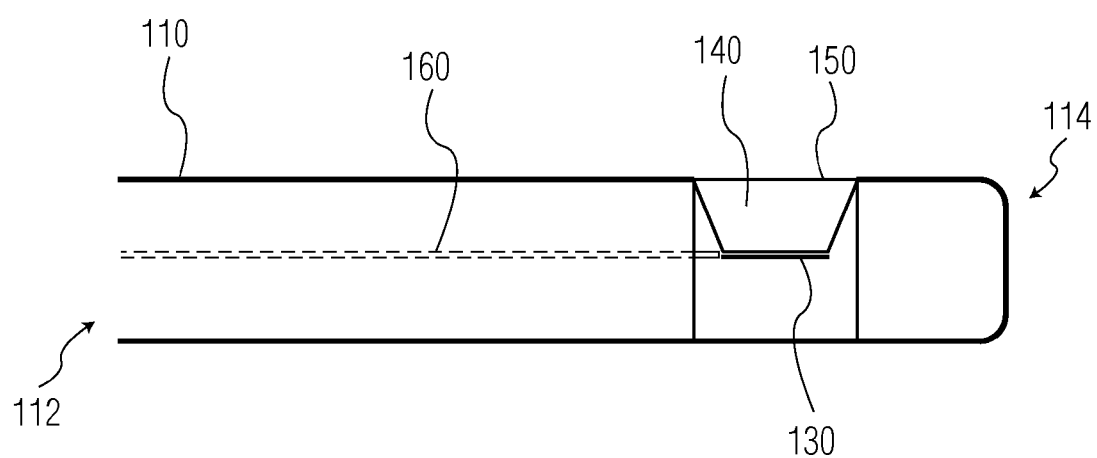

The present invention will now be described more fully hereinafter with reference to the accompanying drawings, in which preferred embodiments of the invention are shown. This invention may, however, be embodied in different forms and should not be construed as limited to the embodiments set forth herein. Rather, these embodiments are provided as teaching examples of the invention. As used herein, the term "acoustic" refers to operation by or with sound waves, including particularly, ultrasonic waves at frequencies above the range of normal human hearing. In the discussion to follow, description is made of catheters, particularly ICE catheters, and associated systems, which include a variably-refracting acoustic lens. In the context of the term "variably-refracting acoustic lens" as used in this application, the word "lens" is defined broadly to mean a device for directing or focusing radiation other than light (possibly in addition to light), particularly acoustic radiation, for example ultrasound radiation. While a variably-refracting acoustic lens may focus an acoustic wave, no such focusing is implied by the use of the word "lens" in this context. In general, a variably-refracting acoustic lens as used herein is adapted to refract an acoustic wave, which may deflect and/or focus the acoustic wave.

Variable-focus fluid lens technology is a solution originally invented for the express purpose of allowing light to be focused through alterations in the physical boundaries of a fluid filled cavity with specific refractive indices (see Patent Cooperation Treat (PCT) Publication WO2003/069380, the entirety of which is incorporated herein by reference as if fully set forth herein). A process known as electro-wetting, wherein the fluid within the cavity is moved by the application of a voltage across conductive electrodes, accomplishes the movement of the surface of the fluid. This change in surface topology allows light to be refracted in such a way as to alter the travel path, thereby focusing the light.

Meanwhile, ultrasound propagates in a fluid medium. In fact the human body is often referred to as a fluid incapable of supporting high frequency acoustic waves other than compressional waves. In this sense, the waves are sensitive to distortion by differences in acoustic speed of propagation in bulk tissue, but also by abrupt changes in speed of sound at interfaces. This property is exploited in PCT publication WO2005/122139, the entirety of which is incorporated herein by reference as if fully set forth herein. PCT publication WO2005/122139 discloses the use of a variable-focus fluid lens with differing acoustic speed of sound than the bulk tissue in contact with the lens, to focus ultrasound to and from an acoustic transducer. However, PCT publication WO2005/122139 does not disclose or teach the application of variable-focus fluid lens technology to one-dimensional acoustic transducer arrays in catheters for intracardiac echocardiography.

Disclosed below are one or more embodiments of an ICE catheter including an acoustic transducer and a variably-refracting acoustic lens having an acoustic interface that is capable of variably refracting acoustic waves.

FIG. 1 illustrates an ICE catheter 100 including an elongated catheter body 110, an acoustic transducer 130, a variably-refracting acoustic lens 140, an acoustically transparent window 150, and an electrical conductor 160. ICE catheter 100 may include one or more other elements such as one or more access ports for supporting a therapeutic device, a guide wire, etc. that may pass through the catheter.

Body 110 has a proximal end 112 and a distal end 114, where ICE catheter 100 is generally inserted into a vein, for example, distal-end first. Body 110 is a tubular structure that may be a flexible or rigid, and for example may be made of plastic.

Beneficially, acoustic transducer 130 comprises a one-dimensional array of acoustic transducer elements. In one embodiment, the transducer elements may include a piezoelectric material, such as lead-zirconate-titanate (PZT), provided on a backing layer or substrate that reflects most of the ultrasonic energy generated by the PZT. The active surface of the PZT may be covered with an acoustic matching layer. Alternatively, acoustic transducer 130 may comprise a single large aperture transducer.

Variably-refracting acoustic lens 140 is adapted to adjust at least one acoustic signal processing characteristic thereof in response to at least one selected voltage applied thereto. For example, beneficially variably-refracting acoustic lens 140 includes the ability to vary an elevation focus of an acoustic wave along the axis of propagation ("focus"), and/or perpendicular to this plane ("deflection"), as described in greater detail below. Further details regarding an embodiment of variably-refracting acoustic lens 140 will be described below with respect to FIGS. 2A-B through FIG. 4.

Acoustically transparent window 150 provides an access port for acoustic waves to pass between variably-refracting acoustic lens 140 and an area where ICE catheter 100 is located, such as the interior of a human heart.

Electrical conductor 160 may include one or a plurality of separate electrically conductive wires for providing various signals and voltages to and from: (1) acoustic transducer 130 and/or variably-refracting acoustic lens 140; and (2) an exterior of ICE catheter 100.

Although in the embodiment of FIG. 1, acoustic transducer 130, variably-refracting acoustic lens 140, and acoustically transparent window 150 are disposed along a sidewall of catheter body 110 near its distal end 114, it should be understood that other configurations are possible. In particular, in some applications an embodiment may be employed where acoustic transducer 130, variably-refracting acoustic lens 140, and acoustically transparent window 150 are disposed at the distal end 114 to produce a so-called "forward-looking" ICE catheter.

Figure 2A:
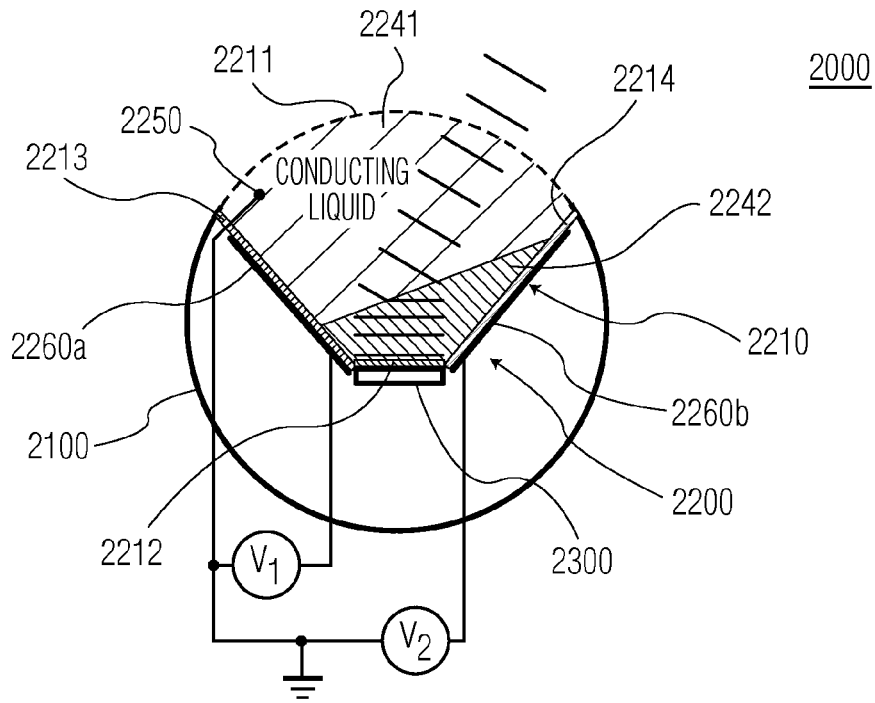
Figure 2B:
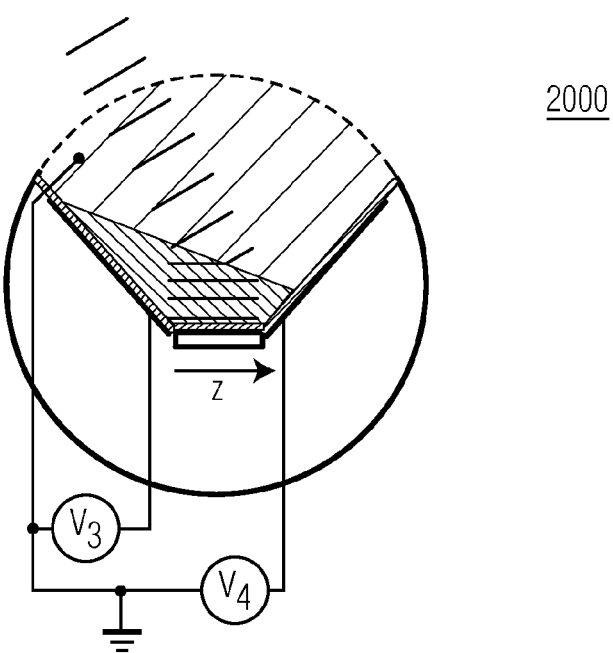

FIGS. 2A-B show a perpendicular cross section view of one embodiment of an ICE catheter 2000 including an acoustic transducer in combination with a variably-refracting acoustic lens. ICE catheter 2000 comprises catheter body 2100, and a variably-refracting acoustic lens 2200 coupled to an acoustic transducer 2300.

Beneficially, variably-refracting acoustic lens 2200 includes the ability to vary elevation focus of an acoustic wave along the axis of propagation ("focus"), and also perpendicular to this plane ("deflection"), as described in greater detail below. Variably-refracting acoustic lens 2200 includes a housing 2210, first and second fluid media 2241 and 2242, first electrode 2250, and second electrodes 2260a and 2260b.

Housing 2210 includes top and bottom surfaces 2211 and 2212, first and second side walls 2213 and 2214, and third and fourth side walls (not shown in FIGS. 2A-B) provided at both ends of first and second side walls 2213 and 2214, and connecting first and second sides 2213 and 2214 together at both ends to define, together with top and bottom surfaces 2211 and 2212, a cavity within housing 2210. Beneficially, top and bottom surfaces 2211 and 2212 of housing 2210 are substantially acoustically transparent, while the acoustic waves do not penetrate through first and second side walls 2213 and 2214 of housing 2210. Acoustic transducer 2300 is coupled to bottom surface 2212 of housing 2210, beneficially by one or more acoustic matching layers (not shown). In one exemplary embodiment, first and second side walls 2213 and 2214 of housing 2210 are formed by covering a corresponding one of the second electrodes 2260a/2260b, for instance, with 10 micrometer of parylene-N (for electrical insulation) and a top-coat (e.g., 10 nm) of an amorphous fluoropolymer (for switching with low hysteresis).

Accordingly, housing 2210 encloses a sealed cavity having a volume in which are provided first and second fluid media 2241 and 2242.

Advantageously, the speeds of sound in first and second fluid media 2241 and 2242 are different from each other (i.e., acoustic waves propagate at a different velocity in fluid medium 2241 than they do in fluid medium 2242). Also, first and second fluid media 2241 and 2242 are not miscible with each another. Thus they always remain as separate fluid phases in the cavity. The separation between the first and second fluid media 2241 and 2242 is a contact surface or meniscus which defines a boundary or interface between first and second fluid media 2241 and 2242, without any solid part. Also advantageously, one of the two fluid media 2241, 2242 is electrically conducting, and the other fluid medium is substantially non-electrically conducting, or electrically insulating.

In one embodiment, first fluid medium 2241 consists primarily of water. For example, it may be a salt solution, with ionic contents high enough to have an electrically polar behavior, or to be electrically conductive. In that case, first fluid medium 2241 may contain potassium and chloride ions, both with concentrations of 0.1 mol·l$^{-1}$, for example. Alternatively, it may be a mixture of water and ethyl alcohol with a substantial conductance due to the presence of ions such as sodium or potassium (for example with concentrations of 0.1 mol·l$^{-1}$). Second fluid medium 2242, for example, may comprise silicone oil that is insensitive to electric fields. Table 1 below lists several exemplary fluids that may be employed as first or second fluid medium 2241 or 2242.

TABLE 1

| Fluid | density (g/cm$^3$) | Speed of sound (km/s) | Attenuation at 5 MHz (dB/cm) |
|---|---|---|---|
| CCl$_4$ | 1.60 | 0.93 | 0.14 |
| Chlorobenzene | 1.1 | 1.3 | |
| Decahydronaphtalene | 0.89 | 1.424 | 0.38 |
| Tetrahydronaphtalene | 0.97 | 1.468 | 0.12 |
| Phenylated silicone oil | 1.1 | 1.37 | 0.4 |
| Water | 1 | 1.5 | 0 |
| Methanol | 0.79 | 1.09 | 0.026 |
| Ethylene glycol | 1.11 | 1.689 | 0.31 |
| Perhydrofluorene | 0.92 | 1.4 | |

Beneficially, first electrode 2250 is provided in housing 2210 so as to be in contact with the one of the two fluid media 2241, 2242 that is electrically conducting, In the example of FIGS. 2A-B, it is assumed the fluid medium 2241 is the electrically conducting fluid medium, and fluid medium 2242 is the substantially non-electrically conducting fluid medium. However it should be understood that fluid medium 2241 could be the substantially non-electrically conducting fluid medium, and fluid medium 2242 could be the electrically conducting fluid medium. In that case, first electrode 2250 would be arranged to be in contact with fluid medium 2242.

Meanwhile, second electrodes 2260a, 2260b are provided at lateral (side) walls 2213 and 2214, respectively of housing 2210. In the embodiment of FIGS. 2A-B, electrodes 2260a and 2260b are connected to two outputs of a voltage generator or variable voltage supply (see FIG. 5) that is external to ICE catheter 2000, and electrode 2250 is connected to ground. Of course, other arrangements are possible, for example where the voltage applied to electrode 2250 is not ground. These and other electrical connections may be provided by means of an electrical conductor 160 disposed within the body 2100 of catheter 2000 (see FIG. 1).

Beneficially, acoustic transducer 2300 comprises a one-dimensional array of acoustic transducer elements. In one embodiment, the transducer elements may include a piezo-electric material, such as lead-zirconate-titanate (PZT), provided on a backing layer or substrate that reflects most of the ultrasonic energy generating by the PZT. The active surface of the PZT may be covered with an acoustic matching layer. Alternatively, acoustic transducer 2300 may comprise a single large aperture transducer.

In one embodiment, ICE catheter 2000 is adapted to both transmit and receive acoustic waves. In that case, in the transmitting mode acoustic transducer 2300 converts electrical signals input thereto into acoustic waves which it outputs. In the receiving mode, acoustic transducer 2300 converts acoustic waves which it receives into electrical signals which it outputs.

In an alternative embodiment, ICE catheter 2000 may instead be adapted to operate in a receive-only mode, with the ultrasonic energy being transmitted from some external device. In that case, a transmitting transducer is provided separately.

Operationally, variably-refracting acoustic lens 2200 operates in conjunction with acoustic transducer 2230 as follows. A lens is formed by the interface, or meniscus, between electrically conducting fluid 2241 and insulating fluid 2242. By applying a force (e.g., a voltage) directly onto at least part of electrically conducting fluid 2241, a displacement of at least part of the interface between fluids 2241 and 2242 is induced and as a result, the meniscus is tilted so as to deflect an applied acoustic beam out of the plane containing the one dimensional transducer array 2300. PCT Publication WO2004051323, which is incorporated herein by reference in its entirety as if fully set forth herein, provides a detailed description of tilting the meniscus of a variably-refracting fluid lens.

In particular, the contact angle of the interfaces with respect to insulated side walls 2213 and 2214 of housing 2210 may be adjusted with voltage(s) or control signal(s) applied to electrodes 2250, 2260a and 2260b. For a certain combination of voltages V1 and V2 applied to electrodes 2260a and 2260b, the interface, or meniscus, between and second fluid media 2241 and 2242 is flat. In the exemplary embodiment of FIG. 2A, when the voltage applied across or between electrodes 2260a and 2260b by the variable voltage supply is a first voltage, $\Delta V_A = V_1 - V_2$, then the interface between first and second fluid media 2241 and 2242 is as shown in FIG. 2A. Meanwhile, because an acoustic wave has different propagation velocities in first and second fluid media 2241 and 2242, the volume filled with first and second fluid media 2241 and 2242 acts to refract the acoustic wave and thereby deflect the acoustic wave in a first direction, for example at an angle $-\alpha$ with respect to a plane extending through the one-dimensional transducer array 2300 along the direction (x-axis in FIG. 3 below) in which one-dimensional transducer array 2300 is aligned, and substantially perpendicular to a plane in which the transducer array 2300 is disposed as defined by the x-axis together with the z-axis shown in FIG. 2B).

When the voltages applied across the electrodes 2260a and 2260b are changed, then the shape of the meniscus will change, due to the electrical field between electrodes 2260a and 2260b. In particular, when the voltage applied across or between electrodes 2260a and 2260b by the variable voltage supply is changed to a second voltage, $\Delta VB=V3-V4$, then the contact surface between first and second fluid media 2241 and 2242 is as shown in FIG. 2B. In that case, first and second fluid media 2241 and 2242 act to deflect the acoustic wave in a second direction, at an angle $+\alpha$ with respect to the plane extending through the one-dimensional transducer array 2300 along a direction (see x-axis in FIG. 3 below) in which one-dimensional transducer array 2300 is aligned. Note that in the case of a symmetric design for the walls 2213 and 2214 of the variably refracting acoustic lens 2200, $\Delta VB=-\Delta VA$.

As different voltages ranging from $\Delta VA$ to $\Delta VB$ are applied across or between electrodes 2260a and 2260b by the variable voltage supply, the acoustic beam will be deflected at corresponding angles ranging from $-\alpha$ to $+\alpha$ with respect to the plane extending through the one-dimensional transducer array 2300 along the direction in which one-dimensional transducer array 2300 is aligned, and substantially perpendicular to a plane in which the transducer array 2300 is disposed. In one embodiment, $\alpha=10$ degrees.

Figure 3:
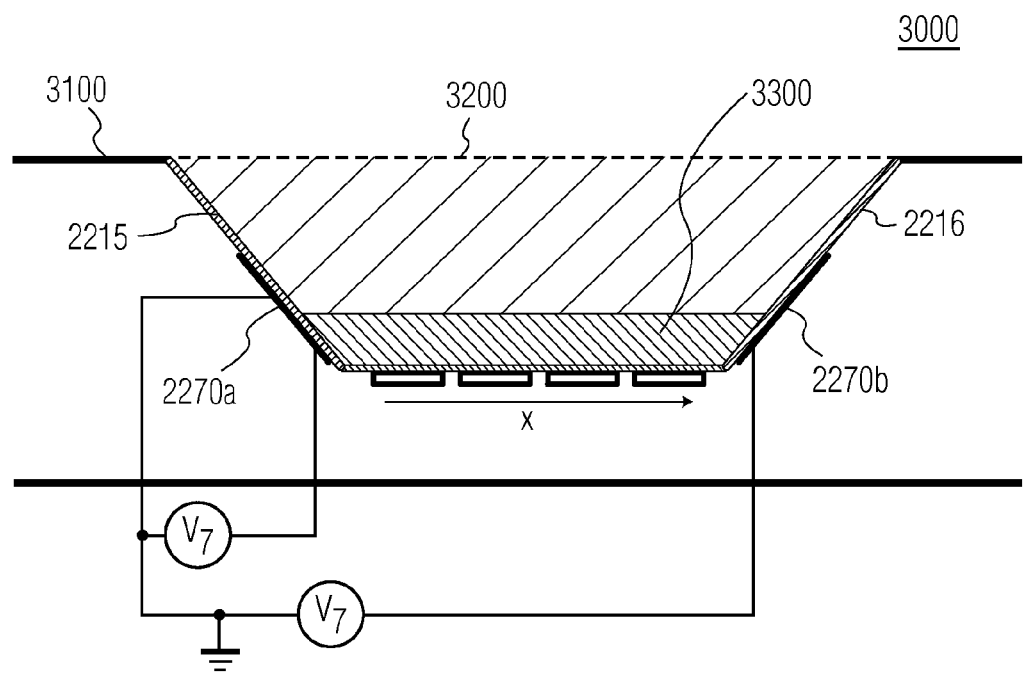
FIG. 3 shows an axial cross section view of one embodiment of an ICE catheter including an acoustic transducer in combination with a variably-refracting acoustic lens.

FIG. 3 shows an axial cross section view of one embodiment of a catheter 3000 including an acoustic transducer in combination with a variably-refracting acoustic lens. ICE catheter 3000 comprises catheter body 3100, and a variably-refracting acoustic lens 3200 coupled to an acoustic transducer 3300. Catheter body 3100, variably-refracting acoustic lens 3200, and acoustic transducer 3300 are generally the same as the corresponding elements in catheter 2000 of FIGS. 2A-B, and so the description of those elements will not be repeated, and only the additional features shown in FIG. 3 will be explained here.

As seen in FIG. 3, variably-refracting acoustic lens 3200 includes a second pair of electrodes 2270a and 2270b disposed at third and fourth side walls 2215 and 2216, which are the third and fourth side walls that connect together first and second side walls 2213 and 2214 to define the cavity in housing 2210, as explained above with respect to FIGS. 2A-B.

Electrodes 2270a and 2270b are used to keep the interface between first and second fluid media 2241 and 2242 flat on the short sides of variably-refracting acoustic lens 3200. Advantageously, third and fourth side walls 2215 and 2216 are tilted as shown, to decrease the voltage required to keep the interface flat.

Beneficially, variably-refracting acoustic lens 3200 has a length along a same direction along which the one-dimensional array is aligned (x-direction in FIG. 3) that is substantially greater than a width in a direction perpendicular to the length of the array (z-direction in FIGS. 2A-B). Consequently, a result of this feature, variably-refracting acoustic lens 3200 can alter the direction in which it transmits and/or receives an acoustic beam in the direction perpendicular to the transducer array (z-direction) while the shape of the acoustic beam remains translationally invariant in the direction along the transducer array (x-direction). Due to this feature, the width of variably-refracting acoustic lens 3200 may be made small, resulting in a fast, full three-dimensional scan.

As an example only, in one embodiment variably-refracting acoustic lens 3200 has a dimension (width) of 3 mm in the dimension perpendicular to the transducer array (y-direction), resulting in a full switching time of 10 ms. For a one dimensional transducer array 3300 consisting of 50-100 elements (at ~5 MHz), two-dimensional scan can be performed in the order of 100 μs. When only an area that is a short distance from the catheter 3000 needs to be imaged (as is often the case in ICE-like applications, where typically a few centimeters depth of field is required), a two-dimensional scan can be recorded as fast as ~35 μs. For a full switch of variably-refracting acoustic lens 3200 in the direction perpendicular to the transducer array (y-direction), the ultrasound beam can be bent over a range of $-\alpha$ to $+\alpha$ with respect to a plane extending through the one-dimensional transducer array 3300 along the direction (x-direction) in which one-dimensional transducer array 3300 is aligned. In one embodiment, $\alpha=10$ degrees. A typical multi-element transducer array 3300 can scan a field of view in the x-direction of ~25 degrees (at the −6 dB points). As a result typically a total field of view of $25*20$ degrees$^2$ can be covered in the order of 250 ms when one requires 5-10 two-dimensional scans at different planes extending through the one-dimensional transducer array 3300 along the x-direction. This allows for three-dimensional ultrasonic imaging with a frame rate of the order of 4 Hz, but this frame rate can be increased further with intelligent drive schemes for variably-refracting acoustic lens 3200 and transducer array 3300.

In one embodiment, an ICE catheter is operated in an ultrasound ablation mode. Since ablation requires high ultrasound intensity it is important that the ultrasound is focused in as small a spot as possible.

Figure 4:
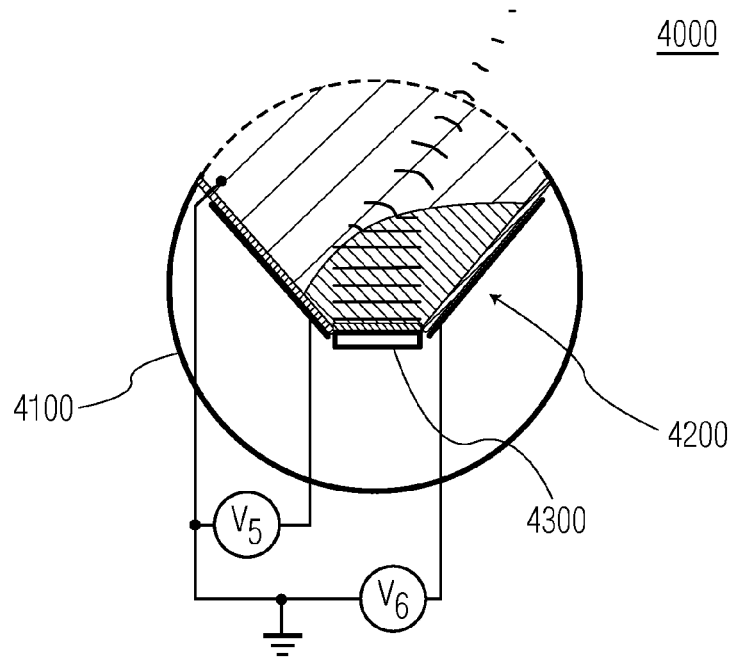
FIG. 4 shows a perpendicular cross section view of one embodiment of an ICE catheter including an acoustic transducer in combination with a variably-refracting acoustic lens adapted to deflect and focus an ultrasonic beam.

FIG. 4 shows a perpendicular cross section view of one embodiment of a catheter 4000 including an acoustic transducer in combination with a variably-refracting acoustic lens adapted to deflect and focus an ultrasonic beam. ICE catheter 4000 comprises catheter body 4100, and a variably-refracting acoustic lens 4200 coupled to an acoustic transducer 4300. Catheter body 4100, variably-refracting acoustic lens 4200, and acoustic transducer 4300 are generally the same as the corresponding elements in catheter 2000 of FIGS. 2A-B and catheter 3000 of FIG. 3, and so the description of those elements will not be repeated, and only the additional features shown in FIG. 4 will be explained here.

In particular, in response to a voltage applied across or between electrodes 2260a and 2260b by the variable voltage supply, $\Delta VC=V5-V6$, then the interface between first and second fluid media 2241 and 2242 is as shown in FIG. 4. As can be seen, the voltage across electrodes 2260a and 2260b is adjusted in such a way that the interface between first and second fluid media 2241 and 2242 becomes curved. Beneficially, fluids 2241, 2242 have a speed of sound chosen to maximize flexibility in the focusing and refraction of the acoustic wave. Accordingly, variably-refracting acoustic lens 4200 is adapted to not only deflect an acoustic beam, but also to focus the acoustic beam. This means that the ultrasound produced by acoustic transducer 4300 can now be focused to a high intensity spot that allows ablation. Beneficially, the geometric gain from the focusing capabilities of variably-refracting acoustic lens 4200 in both the x and y-direction is augmented by the steering capabilities of acoustic transducer 4300 comprising a one dimensional transducer array. By using the focusing capabilities of variably-refracting acoustic lens 4200, it has been experimentally demonstrated that the intensity in the focal point can be increased substantially.

Figure 5:
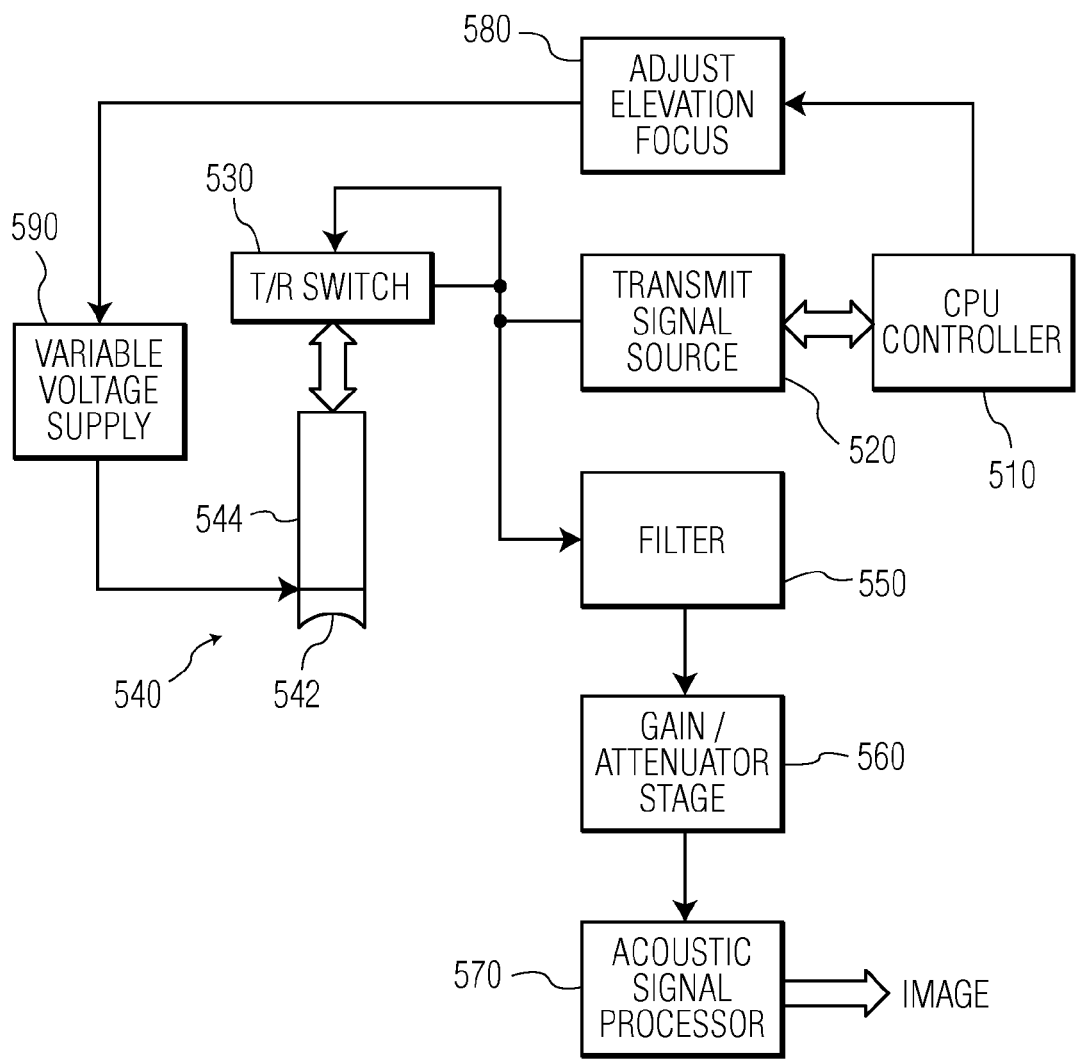
FIG. 5 shows a block diagram of an embodiment of a system including an ICE catheter including an acoustic transducer in combination with a variably-refracting acoustic lens.

FIG. 5 shows a block diagram of an embodiment of a system 500 including an ICE catheter having an acoustic transducer in combination with a variably-refracting acoustic lens. Acoustic imaging system 500 includes processor/controller 510, transmit signal source 520, transmit/receive switch 530, ICE catheter 540, filter 550, gain/attenuator stage 560, acoustic signal processing stage 570, elevation focus controller 580, and variable voltage supply 590. Meanwhile, ICE catheter 540 includes a variably-refracting acoustic lens 542 coupled to an acoustic transducer 544. ICE catheter 540 may be embodied by any of the ICE catheters as shown and described above with respect to FIGS. 1-4.

Operationally, acoustic imaging apparatus 500 operates as follows.

Elevation focus controller 580 controls one or more voltages applied to electrodes of variably-refracting acoustic lens 542 by variable voltage supply 590. As explained above, this in turn controls a refraction angle and/or a focal length of variably-refracting acoustic lens 542.

When the surface of the meniscus defined by the two fluids in variably-refracting acoustic lens 542 reaches the correct topology, then processor/controller 510 controls transmit signal source 520 to generate a desired electrical signal to be applied to acoustic transducer 544 to generate a desired acoustic wave.

In one case, transmit signal source 520 may be controlled to generate short time (broad-band) signals operating in M-mode, possibly short tone-bursts to allow for pulse wave Doppler or other associated signals for other imaging techniques. A typical use might be to image a plane with a fixed elevation focus adjusted to the region of clinical interest. Another use might be to image a plane with multiple foci, adjusting the elevation focus to maximize energy delivered to regions of axial focus. The acoustic signal can be a time-domain resolved signal such as normal echo, M-mode or PW Doppler or even a non-time domain resolved signal such as CW Doppler.

Still another use may be to focus a high energy ultrasonic wave to perform ablation.

In the embodiment of FIG. 5, ICE catheter 540 is adapted to operate in both a transmitting mode and a receiving mode. As explained above, in an alternative embodiment acoustic probe 540 may instead be adapted to operate in a receive-only mode (or even a transmit only mode). In that case, a transmitting transducer is provided separately, and transmit/receive switch 530 may be omitted.

Figure 6:
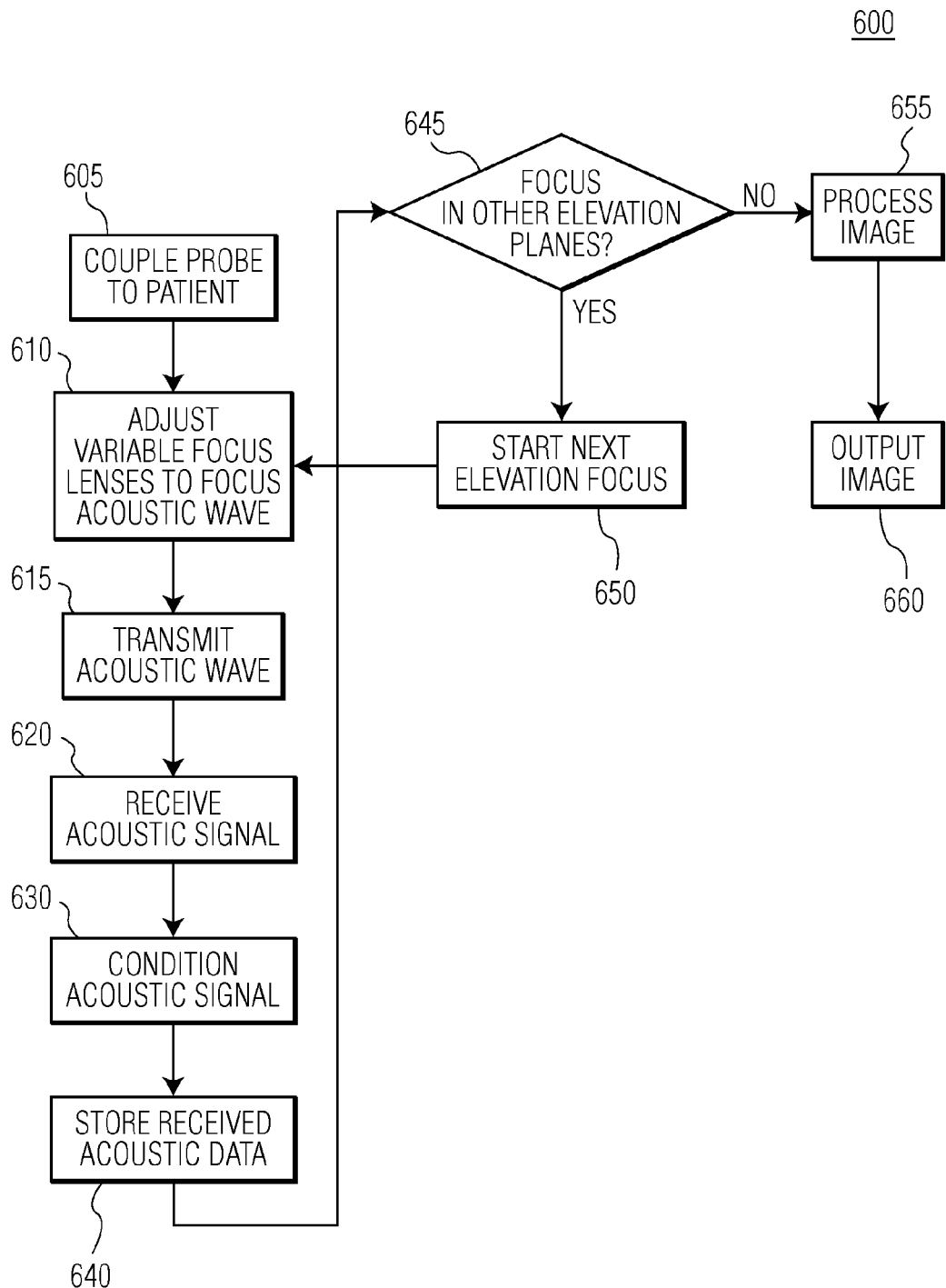
FIG. 6 shows a flowchart of one embodiment of a method of operating an ICE catheter including an acoustic transducer in combination with a variably-refracting acoustic lens.

FIG. 6 shows a flowchart of one embodiment of a method of operating an ICE catheter including an acoustic transducer in combination with a variably-refracting acoustic lens.

In a first step 605, an ICE catheter 540 is introduced into a patient, for example via a vein into the heart.

Then, in a step 610, elevation focus controller 580 controls a voltage applied to electrodes of variably-refracting acoustic lens 542 by variable voltage supply 590 to steer an acoustic beam to a target elevation.

Next, in a step 615, processor/controller 510 controls transmit signal source 520 and transmit/receive switch 530 to apply a desired electrical signal(s) to acoustic transducer 544. Variably-refracting acoustic lens 542 operates in conjunction with acoustic transducer 544 to generate an acoustic wave and focus the acoustic wave in a target area of the patient, including the target elevation.

Subsequently, in a step 620, variably-refracting acoustic lens 542 operates in conjunction with acoustic transducer 544 to receive an acoustic wave back from the target area of the patient. At this time, processor/controller 510 controls transmit/receive switch 530 to connect acoustic transducer 544 to filter 550 to output an electrical signal(s) from acoustic transducer 544 to filter 550.

Next, in a step 630, filter 550, gain/attenuator stage 560, and acoustic signal processing stage 570 operate together to condition the electrical signal from acoustic transducer 544, and to produce therefrom received acoustic data.

Then, in a step 640, the received acoustic data is stored in memory (not shown) of acoustic signal processing stage 570 of acoustic imaging apparatus 500.

Next, in a step 645, processor/controller 510 determines whether or not it to focus in another elevation plane. If so, then the in a step 650, the new elevation plane is selected, and process repeats at step 610. If not, then in step 655 acoustic signal processing stage 570 processes the received acoustic data (perhaps in conjunction with processor/controller 510) to produce and output an image.

Finally, in a step 660, acoustic imaging apparatus 500 outputs the image.

In general, the method 600 can be adapted to make measurements where the acoustic wave is a time-domain resolved signal such as normal echo, M-mode or PW Doppler, or even a non-time domain resolved signal such as CW Doppler.

While preferred embodiments are disclosed herein, many variations are possible which remain within the concept and scope of the invention. Such variations would become clear to one of ordinary skill in the art after inspection of the specification, drawings and claims herein. The invention therefore is not to be restricted except within the spirit and scope of the appended claims.

The invention claimed is:

1. A catheter apparatus, comprising:
an elongated body having proximal and distal ends;
an acoustic transducer disposed proximate the distal end of the elongated body; and
a variably-refracting acoustic lens coupled to the acoustic transducer, the variably-refracting acoustic lens being adapted to adjust at least one acoustic signal processing characteristic thereof in response to at least one selected voltage applied thereto,
wherein the variably-refracting acoustic lens has four side walls and four electrodes disposed on the four side walls, respectively,
wherein at least one electrode of four electrodes partially extends from a bottom of one wall of the four side walls near the acoustic transducer, leaving an exposed portion of the one wall opposite the bottom, the exposed portion being larger than any further exposed portion near the bottom, and
wherein the catheter apparatus further comprises a fifth electrode, wherein the four side walls are between a top surface and a bottom surface of the variably-refracting acoustic lens to form a cavity, wherein the variably-refracting acoustic lens comprises first and second immiscible fluid media disposed within the cavity, and wherein the fifth electrode passes through the exposed portion of the one wall to contact one of the first and second fluid immiscible media.

2. The catheter apparatus of claim 1, wherein
the acoustic transducer is disposed near the bottom surface for transmitting or receiving acoustic signals through the top surface, and
wherein the acoustic transducer includes a plurality of acoustic transducer elements arranged in a one-dimensional array.

3. The catheter apparatus of claim 2, wherein the variably refracting acoustic lens has a length along a same direction along which the one-dimensional array is aligned that is greater than a width in a direction perpendicular to the length, and wherein the variably-refracting acoustic lens is adapted to deflect an acoustic signal applied thereto in a direction that is out of a plane in which the one-dimensional array lies.

4. The catheter apparatus of claim 1, wherein the variably-refracting acoustic lens is adapted to deflect the acoustic signal applied thereto over an angle of at least 10 degrees.

5. The catheter apparatus of claim 1, wherein
a speed of sound of an acoustic wave in the first fluid medium is different than a corresponding speed of sound of the acoustic wave in the second fluid medium, and
wherein the first fluid medium has a substantially different electrical conductivity than the second fluid medium.

6. The catheter apparatus of claim 5, wherein a first electrode of a first pair of electrodes is disposed at a first side wall of the four side walls, and a second electrode of the first pair of electrodes is disposed at a second side wall of the four side walls, where a one-dimensional array of transducer elements is aligned in parallel to a direction of the first and second side walls.

7. The catheter imaging apparatus of claim 6, wherein a first electrode of a second pair of electrodes is disposed at a third side wall of the four side walls, and a second electrode of the second pair of electrodes is disposed at a fourth side wall of the four side walls, where the one-dimensional array of transducer elements extends in a line from the third side wall to the fourth side wall.

8. The catheter apparatus of claim 1, wherein the acoustic transducer consists of a single acoustic transducer element.

9. The catheter apparatus of claim 1, wherein the at least one acoustic signal processing characteristic of the variably-refracting acoustic lens that is adjusted includes at least one of a focus and an elevation of the variably-refracting acoustic lens.

10. The catheter apparatus of claim 1, wherein the variably-refracting acoustic lens and acoustic transducer are disposed along a sidewall of the elongated body.

11. The catheter apparatus of claim 1, wherein the variably-refracting acoustic lens and acoustic transducer are disposed at the distal end of the elongated body in a forward-looking configuration.

12. The catheter apparatus of claim 1, wherein the four side walls are tilted.

13. A catheter apparatus comprising:
an elongated body having proximal and distal;
an acoustic transducer disposed proximate the distal end of the elongated body; and
a variably-refracting acoustic lens adapted to dynamically adjust a direction associated with an acoustic wave coupled to the acoustic transducer, in response to one or more control signals provided thereto,
wherein the variably-refracting acoustic lens has four side walls and four electrodes disposed on the four side walls, respectively,
wherein at least one electrode of four electrodes partially extends from a bottom of one wall of the four side walls near the acoustic transducer, leaving an exposed portion of the one wall opposite the bottom, the exposed portion being larger than any further exposed portion near the bottom, and
wherein the variably-refracting acoustic lens further comprises a fifth electrode, wherein the four side walls are between a top surface and a bottom surface of the variably-refracting acoustic lens to form a cavity, wherein the variably-refracting acoustic lens comprises first and second immiscible fluid media disposed within the cavity, and wherein the fifth electrode passes through the exposed portion of the one wall to contact one of the first and second immiscible fluid media.

14. The catheter apparatus of claim 13, wherein the acoustic transducer includes a plurality of acoustic transducer elements arranged in a one-dimensional array.

15. The catheter apparatus of claim 14, wherein the variably refracting acoustic lens has a length along a same direction along which the one-dimensional array is aligned that is greater than a width in a direction perpendicular to the length, and wherein the variably-refracting acoustic lens is adapted to deflect an acoustic wave in a direction that is out of a plane including the one-dimensional array and perpendicular to its surface.

16. The catheter apparatus of claim 13, wherein the variably-refracting acoustic lens is adapted to deflect the acoustic wave over an angle of 20 degrees.

17. The catheter apparatus of claim 13, wherein
a speed of sound of an acoustic wave in the first fluid medium is different than a corresponding speed of sound of the acoustic wave in the second fluid medium, and
wherein the first fluid medium has a substantially different electrical conductivity than the second fluid medium.

18. The catheter apparatus of claim 17, wherein a first electrode of a first pair of electrodes is disposed at a first side wall of the four side walls, and a second electrode of the first pair of electrodes is disposed at a second side wall of the four side walls, where the one-dimensional array of transducer elements is aligned in parallel to a direction of the first and second side walls.

19. The catheter apparatus of claim 18, wherein a first electrode of a second pair of electrodes is disposed at a third side wall of the four side walls, and a second electrode of the second pair of electrodes is disposed at a fourth side wall of the four side walls, where a one-dimensional array of transducer elements extends in a line from the third side wall to the fourth side wall.

20. The catheter apparatus of claim 13, wherein the acoustic transducer consists of a single acoustic transducer element.

21. The catheter apparatus of claim 13, wherein at least one acoustic signal processing characteristic of the variably-refracting acoustic lens including at least one of a focus and an elevation of the variably-refracting acoustic lens is adjusted.

22. A system, comprising:
a catheter including:
an elongated body having proximal and distal ends;
an acoustic transducer, disposed proximate the distal end of the elongated body; and
a variably-refracting acoustic lens coupled to the acoustic transducer, the variably-refracting acoustic lens being adapted to adjust at least one acoustic signal processing characteristic thereof in response to a selected voltage applied thereto, wherein the variably-refracting acoustic lens has four side walls and four electrodes disposed on the four side walls, respectively;
an acoustic signal processor coupled to the acoustic transducer of the catheter; and
a voltage generator adapted to apply the selected voltage to the variably-refracting acoustic lens of the catheter,
wherein at least one electrode of four electrodes partially extends from a bottom of one wall of the four side walls near the acoustic transducer, leaving an exposed portion of the one wall opposite the bottom, the exposed portion being larger than any further exposed portion near the bottom, and wherein the variably-refracting acoustic lens further comprises a fifth electrode, wherein the four side walls are between a top surface and a bottom surface of the variably-refracting acoustic lens to form a cavity, wherein the variably-refracting acoustic lens comprises first and second immiscible fluid media disposed within the cavity, and wherein the fifth electrode passes through the exposed portion of the one wall to contact one of the first and second immiscible fluid media.

23. The system of claim 22, wherein the voltage generator is adapted to apply a series of voltages so as to deflect an acoustic signal applied to the variably-refracting acoustic lens over a particular angle in a particular number of steps.

24. The system of claim 23, wherein the acoustic signal processor is adapted to generate one or more images in three dimensions in response to the series of voltages applied to the variably-refracting acoustic lens.

25. The system of claim 22, further comprising:
a transmit signal source; and
a transmit/receive switch adapted to selectively couple the acoustic transducer to the transmit signal source, and to the acoustic signal processor.

* * * * *